US009050178B2

(12) United States Patent
Barry et al.

(10) Patent No.: US 9,050,178 B2
(45) Date of Patent: Jun. 9, 2015

(54) JOINT REPAIR USING MESENCHYMAL STEM CELLS

(71) Applicant: Osiris Therapeutics, Inc., Columbia, MD (US)

(72) Inventors: Francis P. Barry, Baltimore, MD (US); J. Mary Murphy, Baltimore, MD (US); Robert Deans, Timonium, MD (US); David J. Fink, Baltimore, MD (US); Annemarie Moseley, Lutherville, MD (US)

(73) Assignee: MESOBLAST INTERNATIONAL SÀRL, Meyrin (CH)

( * ) Notice: Subject to any disclaimer, the term of this patent is extended or adjusted under 35 U.S.C. 154(b) by 0 days.

(21) Appl. No.: 13/743,004

(22) Filed: Jan. 16, 2013

(65) Prior Publication Data

US 2013/0131804 A1 May 23, 2013

Related U.S. Application Data

(63) Continuation of application No. 13/402,444, filed on Feb. 22, 2012, now abandoned, which is a continuation of application No. 12/132,290, filed on Jun. 3, 2008, now abandoned, which is a continuation of application (Continued)

(51) Int. Cl.
*A61F 2/08* (2006.01)
*A61F 2/02* (2006.01)
*A61F 2/38* (2006.01)
*A61F 2/30* (2006.01)
*C12N 5/0775* (2010.01)
*A61K 35/12* (2006.01)

(52) U.S. Cl.
CPC .................. *A61F 2/02* (2013.01); *A61F 2/3872* (2013.01); *A61F 2/30756* (2013.01); *A61K 35/12* (2013.01); *A61K 2035/124* (2013.01); *C12N 2510/00* (2013.01); *C12N 5/0663* (2013.01)

(58) Field of Classification Search
CPC .................. A61F 2/3872; A61F 2/4644; A61F 2002/30756; A61F 2002/30762; A61F 2002/30764; A61F 2002/30766
USPC ..................... 128/898; 623/14.12, 17.16, 908
See application file for complete search history.

(56) References Cited

U.S. PATENT DOCUMENTS 4,642,120 A 2/1987 Nevo et al.
5,053,050 A 10/1991 Itay
(Continued)

FOREIGN PATENT DOCUMENTS

| WO | 97/30662 A1 | 8/1997 |
| WO | 98/51317 | 11/1998 |
| WO | 99/46366 | 9/1999 |

OTHER PUBLICATIONS

Adams et al., Basic and Clinical Foundations, Mow et al., eds., Chap. 2, pp. 15-28, New York, Raven Press (1992).
(Continued)

*Primary Examiner* — Howie Matthews
(74) *Attorney, Agent, or Firm* — McAndrews, Held & Malloy, Ltd.

(57) ABSTRACT

A method of repairing and/or stabilizing a joint by administering mesenchymal stem cells to the joint. Such a method provides for the regeneration of cartilaginous tissue in the joint, including meniscal tissue.

21 Claims, 6 Drawing Sheets

Chondroprotective Repair Meniscus

Related U.S. Application Data

No. 09/841,413, filed on Apr. 24, 2001, now abandoned.

(60) Provisional application No. 60/236,106, filed on Sep. 28, 2000, provisional application No. 60/199,549, filed on Apr. 25, 2000.

(56) References Cited

U.S. PATENT DOCUMENTS

| | | | |
|---|---|---|---|
| 5,206,023 | A | 4/1993 | Hunziker |
| 5,226,924 | A | 7/1993 | Caplan et al. |
| 5,326,357 | A | 7/1994 | Kandel |
| 5,399,493 | A | 3/1995 | Emerson et al. |
| 5,486,359 | A | 1/1996 | Caplan et al. |
| 5,716,616 | A | 2/1998 | Prockop et al. |
| 5,736,396 | A | 4/1998 | Bruder et al. |
| 5,874,500 | A | 2/1999 | Rhee et al. |
| 5,906,934 | A | 5/1999 | Grande et al. |
| 5,908,784 | A | 6/1999 | Johnstone et al. |
| 6,082,364 | A | 7/2000 | Ballan et al. |
| 6,200,606 | B1 | 3/2001 | Peterson et al. |
| 6,482,231 | B1 | 11/2002 | Abatangelo et al. |

OTHER PUBLICATIONS

Bradham et al., Matrix Biology, 14:561-571 (1995).
Brandt, Ann. NY Acad. Sci., 732:199-205 (1994).
Bruder et al., J. Cell. Biochem., 56:283-294 (1994).
Coffin et al., Retroviruses, Cold Spring Harbor Laboratory Press, Cold Spring Harbor, NY, pp. 71-119 (1997).
Ghosh et al., Clin. Orthop., 252:101-113 (1990).
Gillquist et al., Sports Med., 27:143-156 (1999).
Ho et al., Invest. Radiol., 27:84-90 (1992).
Hunziker et al., J. Bone and Joint Surg., 78(5):721-733 (1996).
Joyce et al., J. Cell Biol., 110:2195-2207 (1990).
Little et al., J. Rheumatol., 11:2199-2209 (1997).
Mankin et al., Osteoarthritis: Diagnosis and Medical/Surgical Management, 2nd ed., Moskowtiz, et al., eds., Chap. 5, pp. 109-154, Philadelphia, W.B. Saunders Company (1992).
Murphy et al., Transactions of the 45th Meeting of the Orthopedic Research Society, 24:1035 (1999).
Office Action in U.S. Appl. No. 09/841,413, dated Dec. 14, 2004.
Office Action in U.S. Appl. No. 09/841,413, dated Feb. 11, 2004.
Office Action in U.S. Appl. No. 09/841,413, dated Jan. 12, 2006.
Office Action in U.S. Appl. No. 09/841,413, dated Jun. 4, 2003.
Office Action in U.S. Appl. No. 09/841,413, dated Sep. 10, 2002.
Pettipher et al., Proc. Natl. Acad. Sci. USA, 83:8749-8753 (1986).
Port et al., Am. J. Sports Med., 24(4):547-555 (1996).
Rorvik et al., Acta. Vet. Scand., 37:265-272 (1996).
Setton et al., Bioengineering Conference, BED-vol. 42, pp. 73-74 (Jun. 16-20, 1999).
Setton et al., Clin. Orthop, and Related Res., 367S:S254-S272 (1999).
Sochlaga et al., Cell Transplant, 8(5):511 (1999).
Solursh et al., Dev. Biol., 105:451-457 (1984).
Walsh et al., 42nd Annual Meeting, Orthopaedic Research Society, pp. 100-117 (Feb. 19-22, 1996).
Walsh et al., Tissue Eng., 5(4):327-337 (1999).
Office Action in U.S. Appl. No. 09/841,413, dated Nov. 26, 2003.
Office Action in U.S. Appl. No. 12/132,290, dated May 12, 2011.
Edited by Masanori Fukushima, "Osteoarthritis and neurogenic arthropathy," Merck Manual 17th edition, Japanized version, Nikkei Business Publications, Inc. (Dec. 10, 1999), pp. 452-455.
Tateda et al., Effects of Sodium Hyaluronate (ME3710) in Rabbit Models of Osteoarthritis (OS) and Periarthritis of the Shoulder (PS), Jpn. Pharmacol. Ther., (Apr. 1995), 23(4):833-841.
Office Action in U.S. Appl. No. 12/132,290, dated Dec. 22, 2011.
Office Action in U.S. Appl. No. 12/132,290, dated Jan. 4, 2011.
Office Action in U.S. Appl. No. 13/402,444, dated Oct. 16, 2012.
Agung M et al., Mobilization of bone marrow-derived mesenchymal stem cells into the injured tissues after intraarticular injection and their contribution to tissue regeneration., Knee Surg Sports Traumatol Arthrosc., Jun. 20, 2006, vol. 14 No. 12, pp. 1307-1314.
Pittenger M et al., Adult mesenchymal stem cells: potential for muscle and tendon regeneration and use in gene therapy., J MusculoskeletNeuronal Interac., Jun. 2002, vol. 2 No. 4, pp. 309-320.
Caplan AI and Dennis JE., Mesenchymal stem cells as trophic mediators., J. Cell Bidchem., Aug. 1, 2006, vol. 98 No. 5, pp. 1076-1084.

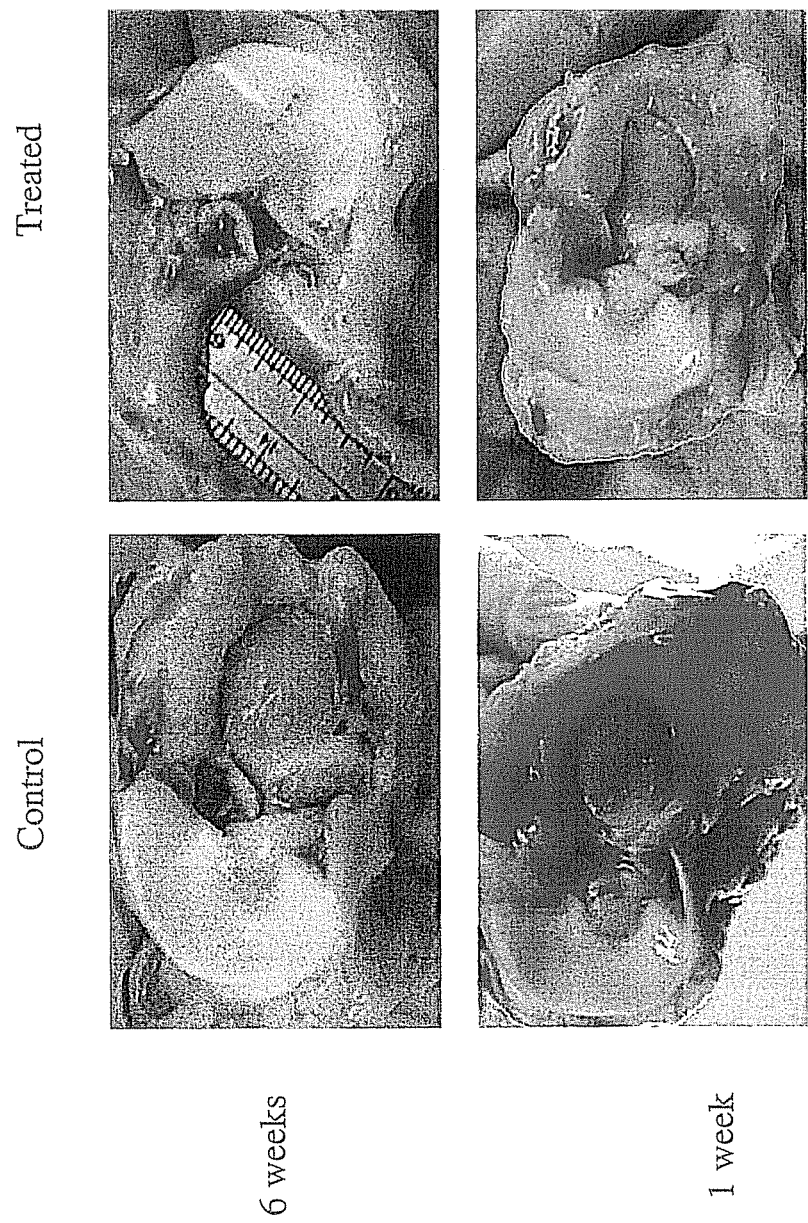

JOINT REPAIR USING MESENCHYMAL STEM CELLS

RELATED APPLICATIONS

This application is a continuation of U.S. patent application Ser. No. 13/402,444 filed on Feb. 22, 2012, and now abandoned, which is a continuation of U.S. patent application Ser. No. 12/132,290 filed on Jun. 3, 2008 and now abandoned, which is a continuation of U.S. patent application Ser. No. 09/841,413, filed on Apr. 24, 2001 and now abandoned, which claims the priority of U.S. Provisional Patent Application Ser. Nos. 60/236,106, filed on Sep. 28, 2000 and 60/199,549, filed on Apr. 25, 2000, the contents of which are incorporated herein by reference in their entireties.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

This invention relates to the repair of joints, which have been injured and/or been subjected to disorders such as osteoarthritis. More particularly, this invention relates to the repair of joints to preventing or reducing subchondral bone sclerosis in a joint, and to preventing damage to the articular cartilage in a joint, and to preventing or reducing the formation of osteophytes in a joint, by administering mesenchymal stem cells to a joint which is in need of repair.

Osteoarthritis is one of the most common diseases of the joint. There is radiological evidence of the disease in approximately 70% of individuals over 65 years, with a slightly higher incidence in females. In the age range of 45-65 years, the incidence approaches 30% of the population (American Academy of Orthopedic Surgeons, 1992). Osteoarthritis is a degenerative disease involving erosion of the articular surface at the ends of bones, leading ultimately to complete loss of the cartilage surface and exposure of the subchondral bone. These changes accompany the onset of severe symptoms including loss of motion, stiffness and joint pain. Articular cartilage, once damaged, does not demonstrate significant self-repair. What little tissue repair occurs is typically fibrous in nature and is an inadequate functional true substitute for articular cartilage. A variety of methods have been investigated to enhance the healing of defects in articular cartilage, with varying degrees of success.

Although osteoarthritis is a major disease affecting a large proportion of the population, the causative factors are unknown. Knee injuries involving the meniscus or the anterior cruciate ligament (ACL) significantly increase the development of radiographic gonarthrosis. Meniscal injury alone results in a 20-fold increase in the risk of developing osteoarthritis. In patients that suffer injury to the ACL or other ligaments in combination with meniscus rupture, there is a very high likelihood that osteoarthritis of the knee will develop. (Gillquist and Messner, *Sports Med.*, Vol. 27, pgs. 143-156 (1999)).

Medial or lateral meniscectomy or ACL resection have been used as a means of creating instability in the knee joints leading to the development of osteoarthritic lesions of large animals such as the sheep (Ghosh, et al., *Clin. Orthop.*, Vol. 252, pgs. 101-113, 1990; Uttle, et al., *J. Rheumatol.*, Vol. 11, pgs. 2199-2209, 1997) and dog (for review see Brandt, *Ann. N.Y. Acad. Sci.*, Vol. 732, pgs. 199-205, 1994). These animals, however, differ from humans with respect to the structure of the articular cartilage layer and subchondral bone and also in the mechanical properties of the tissue. The adult goat has the advantage of being active and having a structural and tissue organization in the stifle joint that compares well with the human knee. There are few reports in the literature demonstrating the use of the; goat as a model for human osteoarthritis. In an early study, involving 4 goats, transection of the anterior cruciate ligament resulted in focal defects on the condylar cartilage (Ho, et al., *Invest. Radiol.*, Vol. 27, pgs. 84-90, 1992). In a more recent study, however, surgical transection of the cruciate ligament failed to produce osteoarthritic changes after 8 months in young, confined goats (Rorvik and Tiege, *Acta. Vet. Scand.*, Vol. 37, pgs. 265-272, 1996).

BRIEF SUMMARY OF THE INVENTION

In an effort to develop reproducible osteoarthritic lesions in the goat stifle, goats were subjected either to ACL resection, medial meniscectomy, or a combination of both procedures. (Murphy, et al., *Transactions of the 45th Meeting of the Orthopedic Research Society*, Vol. 24, page 1035 (1999)). This study was conducted in collaboration with the Tufts University School of Veterinary Medicine. A full spectrum of osteoarthritic changes occurred in the stifles of these animals and the severity of the changes was dependent on the surgical procedure used. The mildest lesions occurred as a result of ACL resection and the most severe lesions occurred as a result of the combined procedure. Medial meniscectomy alone produced moderate lesions. ACL resection resulted in osteophyte formation and other subchondral changes and fibrillation of the cartilage surface primarily on the anterior medial condyle. Medial meniscectomy also induced osteophyte formation and other subchondral changes and cartilage lesions mainly confined to the middle medial condyle. These changes were more severe than those found as a result of ACL resection. Medial meniscectomy in combination with ACL resection resulted in advanced osteoarthritic changes to both hard and soft tissue in the goat stifle after 12 weeks. Cartilage on the unprotected medial tibial plateau also was affected although there is some degree of spontaneous osteoarthritis at this site. There was no repair of the ACL or the medial meniscus in these goats after 12 weeks although there was evident fibrosis as a result of medial meniscectomy. Development of a fibrous meniscal-like tissue was observed in one animal following a combination of ACL resection and medial meniscectomy. This may have been the result of incomplete meniscectomy.

In a second study, the generation of milo osteoarthritic lesions as a result of ACL resection in the goat was investigated further. This procedure is relatively non-aggressive and potentially reversible and as such, presents an additional option for the evaluation of MSC therapy In osteoarthritis. The second study was conducted to validate that the mild osteoarthritic symptoms seen at three months progressed to a more severe form with greater damage to the articular surface at a later time. In this study, goats, which underwent unilateral ACL resection in combination with a mild exercise regime, developed symptoms of osteoarthritis in three months. The symptoms mainly were osteophytic changes with little damage to the cartilage surface. By 6 months, there was more severe chondral damage. This confirmed that the ACL resection in the goat stifle would lead to cartilage changes similar to early osteoarthritis in humans.

Most approaches to treatment of osteoarthritis available today involve control of symptoms with little impact on erosion of the cartilage. Cell therapy offers potential opportunities for intervention by reversing or inhibiting cartilage erosion. A number of approaches are possible that involve either direct implantation of chondrocytes or the delivery of appropriate mitogens or growth factors that may stimulate host chondrocyte proliferation. Other approaches involve the delivery of cell binding or cytotactic factors to enhance the local progenitor cell population, leading ultimately to the reversal of the degradative process. Much of the work in this area has centered around so-called engineered cartilage constructs, i.e., the cultivation of chondrocytes on a biomatrix scaffold in an ex vivo setting, with subsequent delivery of the construct to the lesion site. Other approaches have relied upon the development of procedures involving the fixation of implanted cells beneath a sutured flap of ectopic tissue, either fascia or periosteum. None of these methods, however, is likely to be applicable in mechanically stabilizing the damaged or diseased joint.

In accordance with an aspect of the present invention, there is provided a method of repairing a joint in an animal. The method comprises administering to the joint mesenchymal stem cells. The animal may be a mammal, and in particular, may be a human or non-human primate.

The mesenchymal stem cells may be autologous to the recipient, or may be allogeneic to the recipient.

The mesenchymal stem cells may be obtained by means known to those skilled in the art. For example, the mesenchymal stem cells may be obtained from a bone marrow aspirate, and then expanded in culture. Once expanded in culture, the mesenchymal stem cells are administered to the joint.

The mesenchymal stem cells may be administered to the joint in conjunction with an acceptable pharmaceutical carrier. The selection of a suitable carrier is within the skill of the ordinary artisan. Suitable pharmaceutical carriers include, but are not limited to, hyaluronan, chemically modified hyaluronan, saline, phosphate buffered saline, chondroitin sulfate, glucosamine, mannosamine, proteoglycan, proteoglycan fragments, chitin, chitosan, or other polysaccharide or polymer material.

Applicants have discovered that mesenchymal stem cells, when administered to a joint, provide for the repair and stabilization of a damaged joint, where such damage is due to injury, inflammation, and/or a disease or disorder such as osteoarthritis, for example. The mesenchymal stem cells need not be administered in a scaffold, although a scaffold can be employed. When administered to a joint, the mesenchymal stem cells differentiate into cartilaginous tissue, including meniscal tissue. Although the scope of the present invention is not intended to be limited to any theoretical reasoning, it is believed that the mesenchymal stem cells, when administered to the joint, respond to the destructive forces on the joint, due to the missing and/or damaged tissue, whereby the mesenchymal stem cells differentiate into fibrocartilage tissue. Thus, the mesenchymal stem cells, when administered to a joint, are capable of replacing missing and/or damaged tissue in the joint, including meniscal tissue. Thus, the administration of mesenchymal stem cells to a joint provides for regeneration of cartilaginous tissue, including meniscal tissue, in the joint, thereby providing for repair and stabilization of the joint, as well as reducing pain in the joint and reducing subchondral bone sclerosis.

Thus, the mesenchymal stem cells may be administered to a joint to provide for the repair and stabilization of damaged, injured, or inflamed joints. The damage, injury, or inflammation may be associated with a disease or disorder, such as osteoarthritis, rheumatoid arthritis, gout, reactive arthritis, psoriatic arthritis, or juvenile arthritis, for example. It also may result from an osteoarthrosis or chronic disease of the joint of non inflammatory character.

Joints which may be repaired and/or stabilized, and/or in which inflammation may be reduced, include, but are not limited to, knee joints, hip joints, shoulder jOints, elbow joints, ankle joints, tarsal and metatarsal joints, wrist joints, spine, carpal and metacarpal joints, and the temporal mandibular joint.

The mesenchymal stem cells are administered in an amount effective to repair and/or stabilize a joint in the recipient. In general, the mesenchymal stem cells are administered in an amount ranging from about $1 \times 10^4$ to about $1.5 \times 10^8$, preferably from about $1 \times 10^5$ to about $1 \times 10^8$, more preferably from about $1 \times 10^6$ to about $1 \times 10^7$. The exact number of cells is dependent upon a variety of factors, including, but not limited to, the age, weight, and sex of the patient, the extent and severity of the damage or injury to the joint, or of the disease affecting the joint, the degree of exudation within the joint, the joint space, and other anatomical characteristics that will influence the delivery. Injury to a specific joint may be determined by common medical practice, including but not limited to X-ray and MRI data, visualization by arthroscopy, and the review of a medical history and physical examination of the patient.

BRIEF DESCRIPTION OF SEVERAL VIEWS OF THE DRAWINGS

The invention now will be described with respect to the drawings, wherein:

FIG. 6. Macroscopic appearance of tibial plateau of animals treated with allogeneic cells suspended in a solution of sodium hyaluronan either 1 or 6 weeks following complete medial meniscectomy. Control animals were treated by injection with sodium hyaluronan only. In the treated groups the neomeniscal tissue was detached from the tibial plateau and appeared to provide a bearing surface.

DETAILED DESCRIPTION OF THE INVENTION

Figure 1:
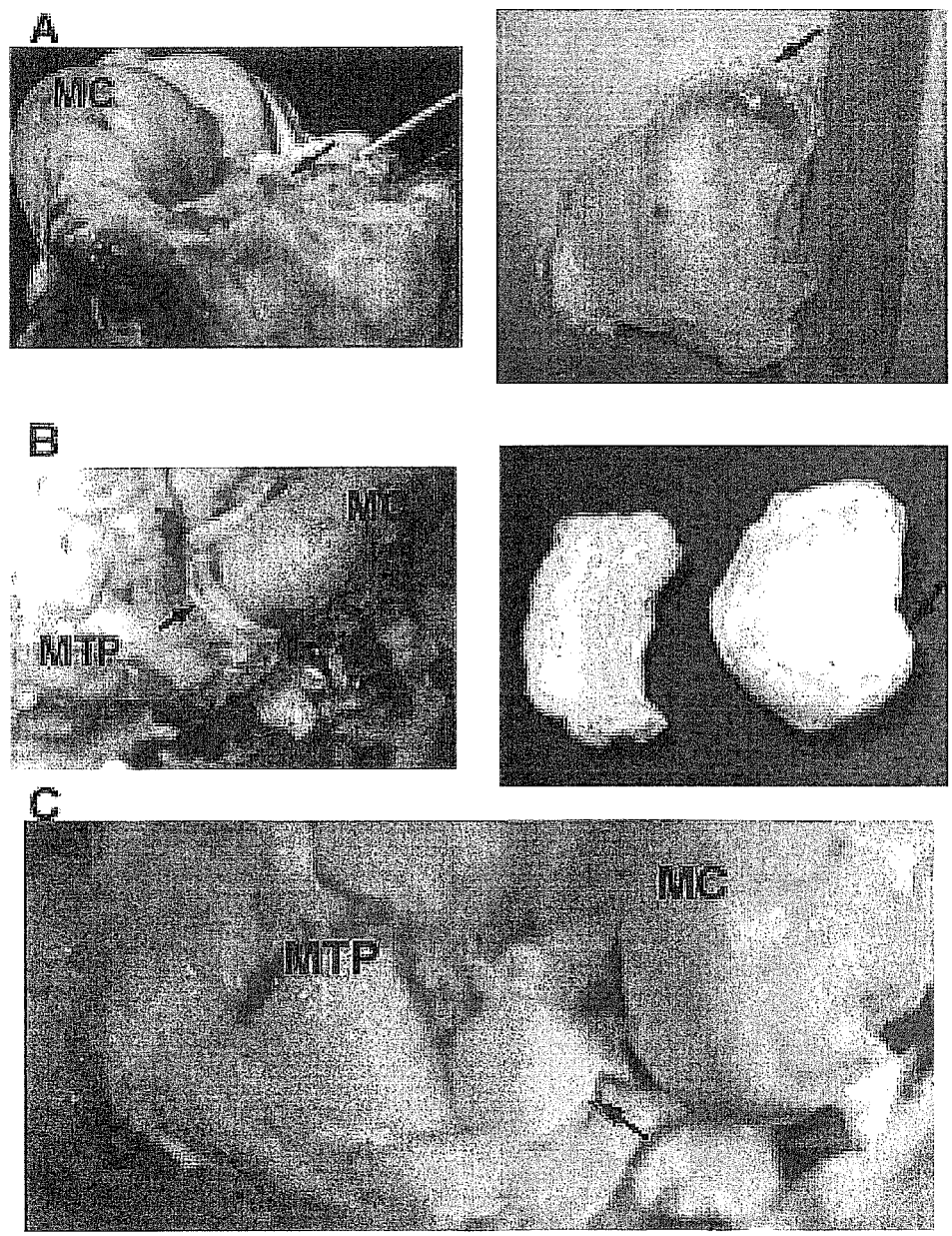
FIG. 1. Effect of MSCs on the formation of meniscal-like tissue in goat knees previously destabilized by a combination of ACL resection and medial meniscectomy. Immature meniscal-like tissue (black arrow) was formed in the area between the medial condyle (MC) and medial tibial plateau (MTP) in knees, previously destabilized by ACL resection and medial meniscectomy and exposed to MSCs, of G151 (A), G154 (B) and G163 (C).

The invention now will be described with respect to the following examples; however, the scope of the present invention is not intended to be limited thereby.

EXAMPLE 1

A total of 12 castrated male Western Cross goats were obtained that were confirmed to be negative for Q fever, brucellosis, and Caprine Arthritis Encephalitis. The goats were randomized into 4 groups that were not different from each other by age or weight. All goats underwent a bone marrow aspiration to obtain mesenchymal stem cells (MSCs) and surgery to create instability in one knee for the development of experimental osteoarthritis. Goats were subjected either to resection of the ACL (n=6) or to total medial meniscectomy (n=6). After a 2 week recovery period, the goats were exercised 5 days each week for 12 weeks. Autologous green fluorescent protein (GFP)-transduced mesenchymal stem cells then were introduced into both operated and contralateral control joints. All goats in each group received injections of 5 ml of a $1 \times 10^6$ cell/ml suspension with (n=3) or without (n=3) high molecular weight hyaluronan (4 mg/ml). The joints were examined upon necropsy after 7 days. In every case, GFP-transduced cells were detected in the synovial fluid and synovial fluid lavage, and were collected from the synovial fluid in a viable state and could be expanded in culture. Fluorescent microscopy revealed that the added cells had colonized and integrated with surface layers of soft tissue within the joint, including meniscus. These observations demonstrated that mesenchymal stem cells can be delivered successfully to an osteoarthritic joint by direct injection, that the cells are retained within the joint, colonize soft tissue surfaces, and can be recovered in a viable form after 1 week.

EXAMPLE 2

A total of 24 castrated male Western Cross goats were obtained that were confirmed to be negative for Q fever, brucellosis, and Caprine Arthritis Encephalitis. The goats were randomized into 4 groups that were not different from each other by age. All goats underwent a bone marrow aspiration to obtain mesenchymal stem cells (MSCs) and surgery to create instability in one knee for the development of experimental osteoarthritis. The groups were shown in Table 1.

TABLE 1

| Group | n | Cell injection | Sacrifice |
|---|---|---|---|
| 1 | 3 | Vehicle only (5 ml) 6 weeks post-op. | 12 weeks post-op. |
| 2 | 6 | GFP-transduced MSCs & vehicle 6 weeks post-op. | 12 weeks post-op. |
| 3 | 6 | Vehicle only (5 ml) 6 weeks post-op. | 26 weeks post-op. |
| 4 | 9 | GFP-transduced MSCs & vehicle 6 weeks post-op. | 26 weeks post-op. |

Groups 1 and 2 were not significantly different with respect to weight (Student's t-test, p=0.68) (Table 2); however, Group 4 was heavier than the corresponding control group (Group 3) (t-test, p=0.001). Goats were group-housed and fed a commercial ruminant diet of grain feed and hay.

The weight of all goats, at surgery to destabilize one stifle, at injection of mesenchymal stem cells, and at sacrifice is given in Table 2 below.

TABLE 2

| Ear tag No. | Osiris Animal No. | Group | Weight at Surgery (kg) | Weight at Injection (kg) | Weight at Sacrifice (kg) |
|---|---|---|---|---|---|
| 350 | G102 | Vehicle alone/12 wk sacrifice | 93.2 | 81.8 | 92.7 |
| 394 | G127 | Vehicle alone/12 wk sacrifice | 82.3 | 67.7 | 76.4 |
| 390 | G143 | Vehicle alone/12 wk sacrifice | 70.0 | 59.6 | 66.4 |
| Mean | | | 81.8 | 69.7 | 78.5 |
| SD | | | 11.6 | 11.2 | 13.3 |
| 367 | G151 | Vehicle + cells/12 wk sacrifice | 86.8 | 76.8 | 84.1 |
| 379 | G154 | Vehicle + cells/12 wk sacrifice | 79.6 | 70.0 | 70.5 |
| 329 | G163 | Vehicle + cells/12 wk sacrifice | 70.9 | 68.2 | 68.6 |
| 336 | G164 | Vehicle + cells/12 wk sacrifice | 75.0 | 65.5 | 64.1 |
| 342 | G165 | Vehicle + cells/12 wk sacrifice | 89.1 | 81.4 | 84.1 |
| 352 | G166 | Vehicle + cells/12 wk sacrifice | 73.6 | 66.8 | 78.2 |
| Mean | | | 79.2 | 71.5 | 74.1 |
| SD | | | 7.4 | 6.3 | 8.3 |
| 324 | G144 | Vehicle alone/26 wk sacrifice | 80.0 | 67.3 | 90.9 |
| 355 | G152 | Vehicle alone/26 wk sacrifice | 84.1 | 64.6 | 80.0 |
| 319 | G153 | Vehicle alone/26 wk sacrifice | 85.5 | 65.0 | 81.4 |
| 302 | G137 | Vehicle alone/26 wk sacrifice | 80.5 | 67.7 | 80.5 |
| 338 | G139 | Vehicle alone/26 wk sacrifice | 85.0 | 72.7 | 94.1 |
| 387 | G094 | Vehicle alone/26 wk sacrifice | 78.2 | 69.6 | 84.1 |
| Mean | | | 82.2 | 67.8 | 85.2 |

TABLE 2-continued

| Ear tag No. | Osiris Animal No. | Group | Weight at Surgery (kg) | Weight at Injection (kg) | Weight at Sacrifice (kg) |
|---|---|---|---|---|---|
| SD | | | 3.0 | 3.0 | 5.9 |
| 326 | G112 | Vehicle + cells/26 wk sacrifice | 97.7 | 79.1 | 97.3 |
| 395 | G114 | Vehicle + cells/26 wk sacrifice | 111.8 | 88.6 | 118.6 |
| 363 | G120 | Vehicle + cells/26 wk sacrifice | 90.9 | 76.4 | 83.2 |
| 392 | G122 | Vehicle + cells/26 wk sacrifice | 100.0 | 80.5 | 93.6 |
| 327 | G131 | Vehicle + cells/26 wk sacrifice | 90.9 | 76.4 | 87.7 |
| 332 | G141 | Vehicle + cells/26 wk sacrifice | 110.9 | 89.1 | 106.4 |
| 389 | G150 | Vehicle + cells/26 wk sacrifice | 79.1 | 64.1 | 80.9 |
| 378 | G167 | Vehicle + cells/26 wk sacrifice | 72.7 | 66.4 | 83.6 |
| 391 | G168 | Vehicle + cells/26 wk sacrifice | 81.8 | 68.6 | 90.9 |
| Mean | | | 92.9 | 76.6 | 93.6 |
| SD | | | 13.6 | 9.0 | 12.3 |

At least two weeks prior to surgery, marrow was aspirated from the iliac crest of each goat and mesenchymal stem cells were isolated and cultured from the aspirates using the following procedure. Marrow was added to Complete Human MSC (hMSC) Medium (low-glucose DMEM containing 10% fetal bovine serum from selected lots, and Penicillin-Streptomycin at 10 mL per liter) and centrifuged to pellet the cells and remove the fat layer. The cells were washed with medium and plated on culture dishes at 100,000-400,000 cells/cm$^2$. All preparations were cultured AT 37° C. in a humidified atmosphere containing 5% $CO_2$. Non-adherent cells were removed 3-5 days after plating at the time of the first medium change, and the medium was changed twice weekly thereafter. When culture dishes became almost confluent, cells were detached with 0.05% (w/v) trypsin containing 1 mM EDTA for 5 min at 37° C. For subculturing, MSCs were plated in T-185 flasks at 0.5-1.0×10$^6$ cells per flask in 35 mL Complete hMSC Medium. MSCs not immediately used were cryopreserved by freezing in MSC Freezing Medium (40 ml of Complete MSC Medium, 5 ml of FBS, and 5 ml of DMSO).

Human MSCs may be isolated and cultured according to the method disclosed in U.S. Pat. No. 5,486,359. Human MSCs also may be purchased from BioWhittaker (Walkersville, Md.). The use of allogeneic MSCs is discussed in PCT Application No. PCT/US99/05351.

Instability of one stifle in each goat was created by surgical resection of the ACL and medial meniscectomy. On the day prior to surgery, feed was removed and just prior to surgery the goats were anesthetized with torbutrol (pre-analgesic) and a ketamine and diazepam cocktail (for induction). One hind limb was clipped from tarsus to the level of the coxofemoral joint and cleaned in an aseptic manner. The animal was transported to the operating room and anesthetized using isofluorane where a final sterile preparation was performed using a hanging leg technique. The leg was draped using towels and the distal foot wrapped in sterile towels and vetwrap. A lateral arthrotomy was performed and the anterior (cranial) cruciate ligament was excised from its attachment on the medial aspect of the lateral femoral condyle using a #11 blade. This proximal attachment was brought forward (anterior) and the entire cruciate ligament was excised from its tibial attachment. The caudal horn of the meniscus was grasped with hemostat and its axial (lateral) attachment was excised from its tibial attachment. Working from caudal to lateral, then cranial, the meniscus was excised from attachments until it was completely removed. The stifle was moved in a drawer test to assure that the entire cruciate ligament had been excised. The joint capsule was closed using absorbable synthetic suture material (examples include Vicryl, PSD, Dexon, Maxon, etc.) in a simple continuous or cruciate pattern. The lateral fascia was closed using 0 or 2-0 absorbable synthetic suture material in a continuous pattern. The subcutaneous tissues were closed using 2-0 absorbable synthetic suture material in a subcuticular pattern. The skin was closed using skin staples.

Analgesics were given twice a day for three days, postoperatively. The incision was monitored for signs of infection, including redness, exudate, and excessive swelling. The skin staples/sutures were removed in two weeks. After a recovery period of two weeks, all animals were exercised for five days a week until sacrifice. The exercise regimen consisted of a run approximately 90 m in length.

Preparation of Transduced MSCs for Injection into the Knee Joint

The plasmid pOT24, which includes a polynucleotide sequence encoding GFP protein, was transfected into the GP+E86 packaging cell line, and virus was produced by the modified GP+E86 cells. This virus then was transduced into the PG13 packaging cell line, and virus was produced by the modified PG13 cells.

MSCs, cryopreserved at the end of primary culture, were thawed and transduced with retrovirus produced from the PG13 (mouse 3T3-based) packaging cell line containing a gibbon-ape envelope (Coffin et al. *Retroviruses*, Cold Spring Harbor Laboratory Press Cold Spring Harbor, N.Y., pgs. 71-119, 1997). The virus carried the sequence for the enhanced green fluorescent protein of the jellyfish *Aequorea victoria*. The standard transduction was performed as follows: goat mesenchymal stem cells were cultured at 37° C. in 5% $CO_2$ in air overnight in T80 flasks after which. the culture medium in each flask was replaced with 15 mL of transduction cocktail for centrifugal transduction, after which 2 mL of fresh medium was added and the incubation continued. Centrifugal transduction was performed as follows: culture medium in each flask was replaced with 15 mL of transduction cocktail and centrifuged in a Beckman GS-6R centrifuge using flask carriers at different centrifugal forces and duration at 32° C. Following centrifugation, 15 mL of fresh medium was added to each flask. A second transduction protocol was performed the following day. Cells were selected in G418 at a concentration of 1.0 mg/mL and maintained in culture. After G418 selection the transduced MSCs were expanded to the end of passage 2 (P2) culture, and trypsinized and frozen until required for injection. Transduction efficiency was determined using flow cytometry prior to cryopreservation.

Vials containing the cryopreserved transduced goat MSCs were thawed rapidly at 37° C. and added to 40 ml of hMSC Complete Medium. The cells were centrifuged for 5 min at 1500 rpm and 20° C. and resuspended in 5 ml PBS. 50 µl cell suspension was removed for determination of viable cell count using Trypan Blue. A total of 10×10⁶ cells were washed with 20 ml PBS twice and resuspended in 5 ml of 4 mg/ml Hyalartin V (Pharmacia) using a 12-ml syringe with an 18 G needle attached. The cell suspension was aspirated into the syringe for injection into the goat knee and 1-ml PBS added to the tube for washing.

Injection of Transduced Goat MSCs into the Goat Stifle

The goats were weighed and blood was collected to obtain serum. The knee area was shaved and the goats were anesthetized and intubated. After acquiring cranial to caudal and lateral radiographs of both knees, the goat was placed in dorsal recumbency with the knee to be injected held up. The area around the knee was sterilized and the knee was flexed and extended 20 times to circulate synovial fluid. With the knee placed in 70-90° flexion, as much fluid as possible was aspirated from the joint and retained for analysis. With the knee in the same position, 10-20 ml PBS was injected into the joint laterally. An 18 G needle was inserted just proximal to the meniscus and posterior to the lateral edge of the patellar ligament, through the triangle formed by the epicondyle of the femur, the meniscal/tibial plateau and the notch formed by their junction. After flexing and extending 20 times the lavage was aspirated from the joint and retained. A three-way stopcock with an 18 G needle attached was inserted into the triangle described above on the medial side of the joint, just medial to the patellar ligament. With the stopcock in the open position, the syringe containing the cell suspension prepared as described above was attached to the stopcock and the cell suspension injected into the joint capsule. Any suspension remaining in the stopcock was washed with 1 ml PBS. The joint was flexed and extended 20 times and the goat was maintained in this position for at least 10 min before recovery and transfer to the holding pen.

Goat Necropsy and Tissue Collection

Group 1 and 2 goats were sacrificed six weeks after injection of transduced cells into the joint. The popliteal and inguinal lymph nodes were collected from both operated and contralateral control limbs before disarticulation at the hip. Radiographs were taken and synovial fluid was collected without lavage and also after a 10 ml PBS lavage. After aspirating the lavage the joint was dissected and the following tissues collected: joint/synovial capsule lining, fat pad, extensor digitorum longus tendon, posterior cruciate ligament and lateral meniscus. Any repair medial meniscal tissue was also collected.

After dissection, 13 areas of cartilage on both the operated and contralateral control joints and both joints of control animals were graded visually using the grading system described in Table 3 below.

TABLE 3

| Score | Description |
| --- | --- |
| <0.5 | Within normal limits. |
| 0.5 | Minor roughness. |
| 1.0 | Chondromalacia evident but not severe. |
| 1.5 | Erosion of cartilage with fibrillation. Severe chondromalacia. |
| 2.0 | Defined lesion. No exposure of subchondral bone |
| 2.5 | Exposure of subchondral bone. Advanced lesion. |
| 3.0 | Complete degradation of cartilage. |

The selected areas were located on the protected and unprotected sections of the medial and lateral tibial plateaus, the anterior, middle and posterior sections of the medial condyle, the middle and posterior sections of the lateral condyle, the lateral, central and medial sections of the trochlear ridge and on the patella. Using a scalpel, cartilage samples from the middle and lateral medial condyles, and from the unprotected area of the medial and lateral tibial plateaus were obtained. Portions of all tissues collected were snap frozen for molecular analysis and fixed in formalin for histological analysis. The joints also were fixed in formalin. All joints were photographed prior to fixation and photographed and re-examined after fixation to confirm grading scores and to note the presence of osteophytes. The distance between the medial and lateral trochlear ridges was measured and expressed as the Trochlear Distance (TRD). Segments of the middle and lateral medial condyles, and the unprotected area of the medial and lateral tibial plateaus were cut using a saw and both decalcified and embedded in paraffin for histological analysis or embedded in methyl methacrylate without decalcification. Some contralateral joints were treated in the same manner as the operated joint and evaluated as control tissues.

Radiography

Radiography was performed prior to initial surgery, at injection, and at sacrifice.

Results and Discussion

At 3-month sacrifice, all operated joints (Groups 1 and 2, Vehicle only, and + Cells) were fibrotic and effused. Synovial fluid volumes as an indication of the extent of the effusion, cartilage score, and the TRD as an indication of subchondral changes or osteophyte broadening of the trochlear groove are given in Table 4 below.

TABLE 4

| Goat ID | Group | Effusion (Syn. Fluid Volume ml) | TRD (% increase over control joint) | Cartilage Score on Middle Medial Condyle (Scale 0-3) | Meniscal-Like Structures |
| --- | --- | --- | --- | --- | --- |
| G102 | Vehicle | 8.6 | 19.7 | 2.0 | No visible repair of the medial meniscus (MM) |
| G127 | Vehicle | 3.5 | 14.1 | 2.0 | Anterior fibrous MM repair tissue sampled and fixed. |
| G143 | Vehicle | 6.0 | 24.4 | 2.0 | Anterior fibrous MM repair tissue sampled and fixed. |
| G151 | +Cells | 4.0 | 11.5 | 2.0 (Small Lesion) | Vascularized meniscus-like mass found over the unprotected area of the medial tibial plateau. Opaque, glistening. |

TABLE 4-continued

| Goat ID | Group | Effusion (Syn. Fluid Volume ml) | TRD (% increase over control joint) | Cartilage Score on Middle Medial Condyle (Scale 0-3) | Meniscal-Like Structures |
|---|---|---|---|---|---|
| G154 | +Cells | 1.4 | 9.3 | 1.0 | Anterior and posterior repair of medial meniscus. Posterior piece-opaque, glistening. |
| G163 | +Cells | 6.5 | 2.8 | 1.5 | Anterior and posterior repair of medial meniscus. Posterior piece-opaque, glistening. |
| G164 | +Cells | 7.0 | 3.2 | 2.0 | Anterior and posterior repair of medial meniscus. Posterior piece-opaque, glistening but small and not organized. |
| G165 | +Cells | 10.5 | 20.5 | 1.0 | Meniscal-like material on the protected medial tibial plateau, anterior and posterior. Laying on top of bony, calcified mass on the posterior medial tibial plateau. |
| G166 | +Cells | 10.0 | 18.6 | 2.5 (3.0) | Anterior and posterior repair of medial meniscus. Posterior piece-opaque, glistening but small and not organized. |

All operated joints showed osteophyte formation.

In four of the six knees that were treated with MSCs the amount of osteophyte formation was lower. Osteophyte formation at other sites on the joint in these goats also was lower when compared to knees exposed to hyaluronan alone. In all cases there was severe osteophyte formation on the posterior medial tibial plateau; however, the newly formed surface in the knees exposed to MSCs seemed to be smoother and hematoma was noted at this site in the case of two of the three vehicle-only goats. In the case of G165 (MSCs and vehicle) the osteophyte manifested itself as a mass of hard, calcified tissue (31.2 mm×41.29 mm×23.65 mm) topped by a meniscal-like structure. All contralateral joints were normal in appearance and showed no effusion at sacrifice.

In all six '+MSC' goats there was tissue with the appearance of "immature meniscus" covering some of the exposed part of the medial tibial plateau, and in 3 cases this tissue was organized. FIGS. 1A, 1B, and 1C show the appearance and location of the repair tissue for G151, G154 and G163, respectively. In these cases the newly regenerated tissue occupied a slightly posterior location in the joint because of the altered mechanical environment. In the two cases where the tissue was most organized and not as posterior on the joint (G154 and G163), there appeared to be some protection of the cartilage on the middle medial condyle and less osteophyte formation on the femoral condyle and groove indicating less sever osteoarthritis. In the case of G151 there also seemed to be some protection with a much smaller lesion formed. In these cases, the degree of effusion and the change in TRD were minimal (Table 4). Thus, the immature meniscal-like tissue was regenerated in an area that cushioned the opposing surfaces of the medial condyle and medial tibial plateau and protected the joint from developing osteoarthritis as a result of the altered mechanical loading in these joints.

Figure 2:
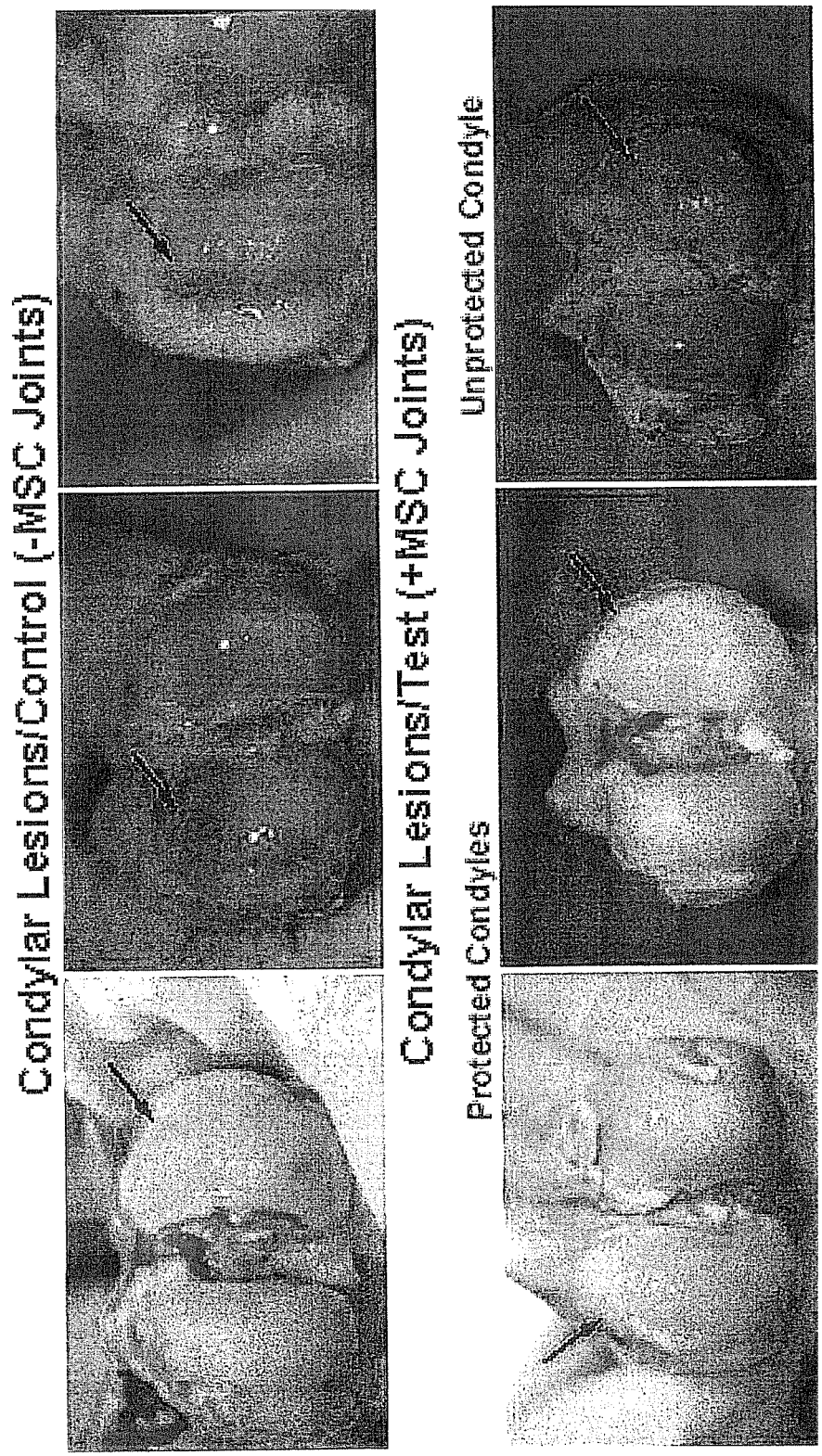
FIG. 2. Effect of MSCs on the development of cartilage lesions on the middle medial condyle in goat knees previously destabilized by a combination of ACL resection and medial meniscectomy. Cartilage lesions graded as described in Table 2 and with scores indicated in Table 3 developed on the middle medial condyle of vehicle-only goats (G102, G127, and G143, top panel left, middle and right images, respectively). MSCs injected along with the vehicle prevented the development of severe lesions at this site in several animals, for example, in the case of G151 (bottom panel, middle image) but not in all cases, as in the case of G166 (bottom panel, right image).

In one case (G166) the repair tissue did not protect the articular surfaces, as it formed too posterior on the medial tibial plateau. FIG. 2 shows the degree of protection afforded by the meniscal-like tissue in G151 and G154 (bottom panel). Cartilage damage was significantly less in these joints, which had been injected with MSCs, compared to that found in vehicle-only joints (FIG. 2, top panel). Osteophyte formation on the medial aspect of the medial condyle also was significantly less in these MSC injected joints compared to 'Vehicle Only' goats (FIG. 2). Limited fibrous, poorly organized, meniscal repair was observed in 2 of 3 'Vehicle Only' goats on the anterior aspect of the joint. In neither case was the mass or degree of organization as significant as that observed in the '+Cells' group, and there was no apparent protection of the joint as indicated by the Cartilage Score (Table 4).

The above results show that autologous mesenchymal stem cells infused into arthritic stifles of goats, six weeks after combined medial meniscectomy and ACL resection, stimulated the production of meniscus-like tissue in the joints of 4 out of 6 goats sacrificed six weeks post infusion. No similar tissue was observed in the joints of 3 goats infused with carrier only.

In the joints in which the meniscus-like tissue was observed, the course of the progressive destruction of hyaline cartilage on the articular surface was slowed, based on gross scoring of the joint surface; i.e., the injection of mesenchymal stem cells prevented the rapid destruction of the joint cartilage. This effect was not observed in the carrier-only control joints. Other changes, joint effusion, and broadening, also were decreased in the MSC-infused group, which is consistent with the protective effect of the mesenchymal stem cells treatment. These observations show that mesenchymal stem cells, when injected into arthritic joints in the goat stifle, are retained in the joint for a sufficient period to have a therapeutic effect. In the results summarized here, injected mesenchymal stem cells stabilized the joint and protected the articular surfaces against the progressive degeneration observed in control joints.

Figure 3:
FIG. 3. Gross appearance of tissue 6 months post-surgery. Gross appearance of the tibial surfaces with menisci attached (A and C) and the anterior and middle medial condyle (B and D) of an osteoarthritic goat knee injected with HA (A and B) and with GFP-transduced MSCs plus HA (C and D). Arrows indicate the meniscal neotissue formed in a joint exposed to MSCs and to a synovial-like proliferation noted in a control goat knee. Asterisk indicates osteophyte formation.

In 4 out of 6 goats at 3 months and in 7 out of 9 goats at 6 months, the generated meniscal-like tissue was somewhat organized with a hyaline-like appearance. (FIG. 3C.) No similar tissue was observed in the joints of the 3-month control goats infused with HA alone; however, thin synovial proliferation was noted in the 6-month control joints (FIG. 3A). This tissue was found posterior to the weight-bearing area of the destabilized osteoarthritic joint.

In those joints where organized meniscal-like tissue was observed, the progressive destruction of cartilage on the articular surface was slowed, based on gross scoring of the joint surfaces. FIG. 3B shows the appearance of the medial condyle of a 6-month control goat with complete degradation of articular cartilage across the entire surface and repopulation of the area with osteophyte. Protection of this surface was noted in test joints exposed to MSCs (FIG. 3D). This effect was not observed in the vehicle only, control joints. Other changes such as joint effusion, osteophyte formation on the femoral condyle and joint broadening also were reduced, consistent with the protective effect of the MSC treatment.

Figure 4:
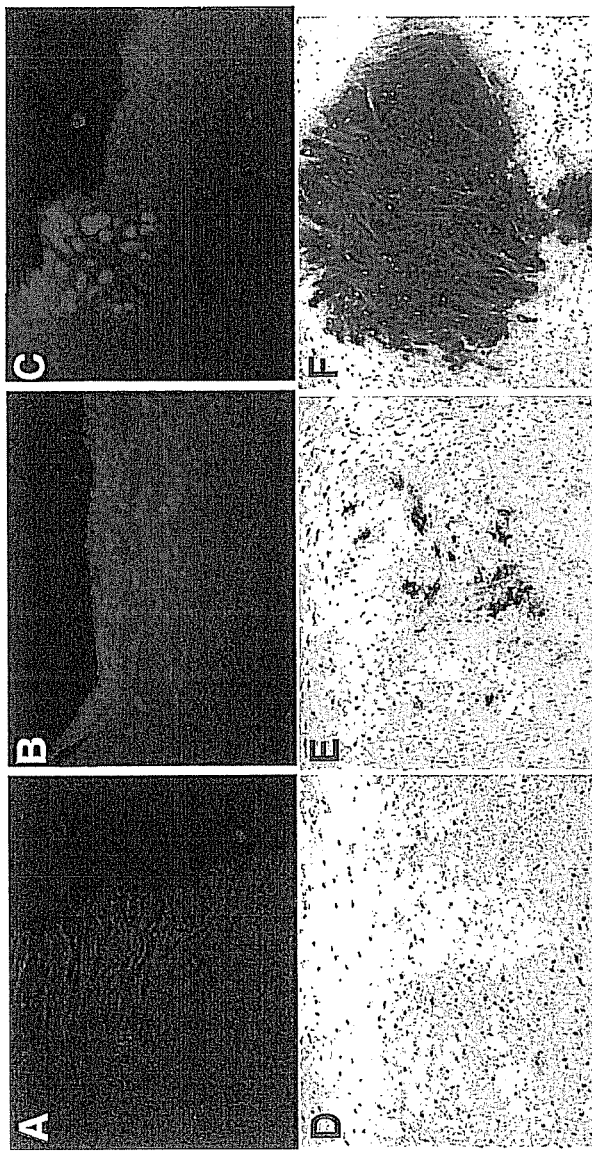
FIG. 4. Histological Analysis of Meniscal Neotissue. Fluorescence micrographs of meniscal tissue show GFP-positive cells at the condylar surface of the meniscal neotissue (B and C). A negative micrograph was taken of the posterior of the cut tissue not exposed to the joint environment. Cells in the center of the tissue bound the anti-Type II collagen antibody (D through F). Original magnification was 200× for A through E and 100× for F.

Examination of the organized meniscal neotissue at 3 months by fluorescence microscopy indicated the presence of GFP-positive cells at the surface of the tissue (FIGS. 4B and 4C). Immunohistochemical staining of the posterior meniscal-like tissue induced a dense, cellular Type I collagen-positive, fibrous network (not shown) with small areas of more rounded cells that were Type II collagen-positive (FIGS. 4D through 4F).

For the 6-month animals, the extent of damage, based on cartilage surface scores, is greater in the control goats than those that received the mesenchymal stem cells, as shown in Table 5.

TABLE 5

| Eartag # | Goat # | Weight (Kg) | Group | Middle Medial Condyle | | | Synovial | |
|---|---|---|---|---|---|---|---|---|
| | | | | Lesion Size (mm) | Cartilage Score | Note | Proliferation (pinkish) | Whitish Hyaline-like |
| 324 | G144 | 90.91 | Vehicle | 20.9 × 8.9 | 3.5 | Osteophyte in lesion | | Yes, attached to MTP |
| 355 | G152 | 80.0 | Vehicle | 18.9 × 10.7 | 3.5 | Osteophyte in lesion | Yes | |
| 319 | G153 | 81.36 | Vehicle | 27.9 × 14.6 | 3.5 | Osteophyte in lesion | Yes | |
| 302 | G137 | 80.45 | Vehicle | 15.6 × 2.6 | 3.5 | Osteophyte in lesion | Yes | |
| 338 | G139 | 94.09 | Vehicle | 22.5 × 11.5 | 1.5 | | | Small |
| 387 | G094 | 84.09 | Vehicle | 17.7 × 11 | 3.5 | Osteophyte in lesion | Yes | |
| Mean/SD | | | | | 3.17 | 0.82 | | |
| 326 | G112 | 97.27 | Cells | 22.7 × 11.3 | 3.5 | Osteophyte in lesion | | Yes |
| 395 | G114 | 118.64 | Cells | 17.5 × 12.3 | 2.5 | | Yes | |
| 363 | G120 | 83.18 | Cells | 12.3 × 7.7 | 1 | | | Yes |
| 392 | G122 | 93.64 | Cells | 25.4 × 11.3 | 2.5 | | | V. Small |
| 327 | G131 | 87.73 | Cells | 14.5 × 10.4 | 2 | | | Yes |
| 332 | G141 | 106.36 | Cells | 24.9 × 12 | 2 | | | Small |
| 389 | G150 | 80.91 | Cells | 11.5 × 4.5 | 1.5 | | | Yes |
| 378 | G167 | 83.64 | Cells | 10 × 6 | 1 | | | Yes |
| 391 | G168 | 90.91 | Cells | 15.4 × 8.9 | 2 | | | Yes |
| Mean/SD | | | | | 2.0 | 0.79 | | |

One application of the discovery is the reduction of pain by way of meniscal tissue regeneration between opposing bone or osteochondral surfaces.

Another application of the above results is to forestall or eliminate the need for joint replacement. Still another application is the reduction of inflammation in a damaged or diseased joint, thus leading to the reduction of pain and to the restoration of function of the joint.

EXAMPLE 3

Figure 5:
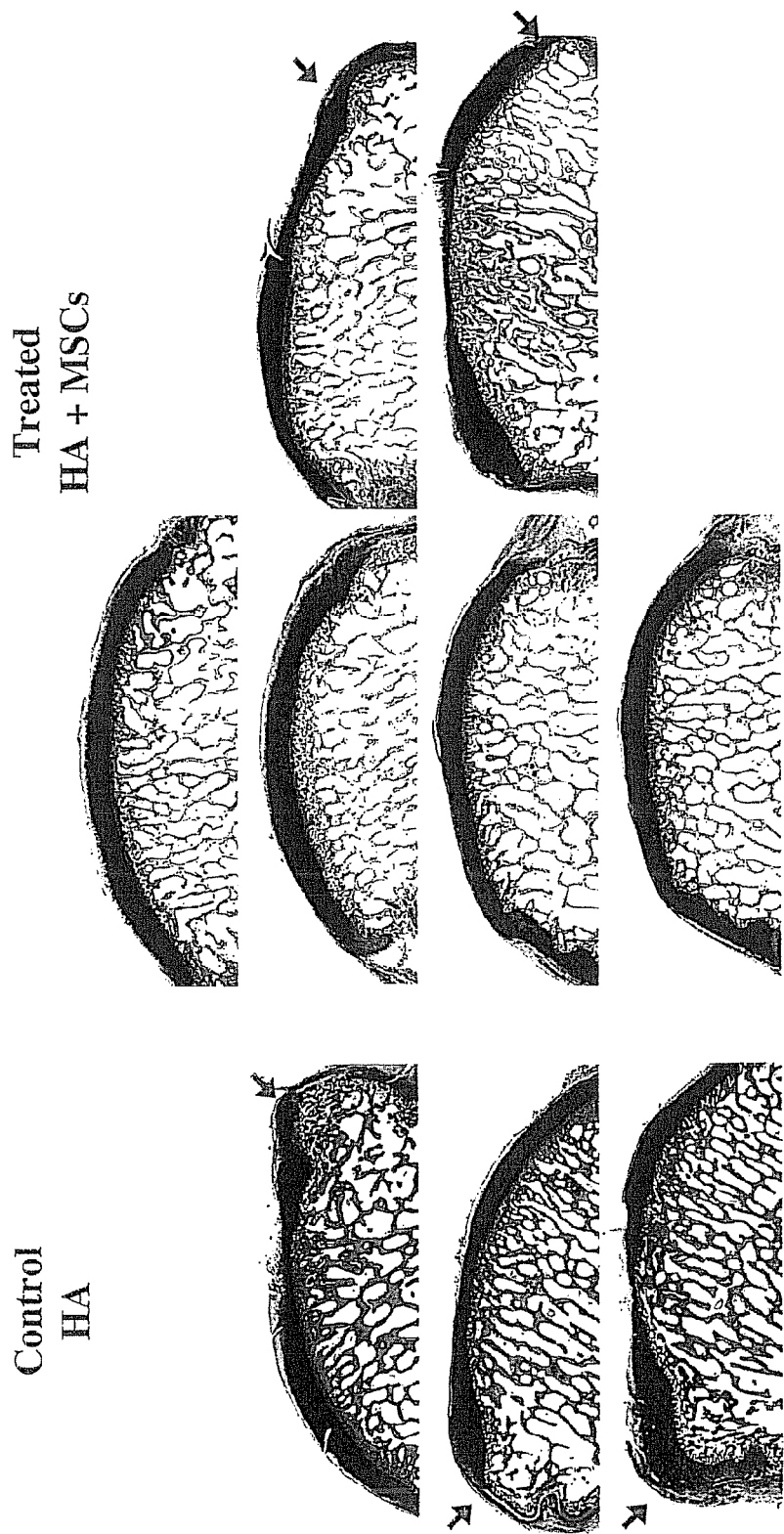
FIG. 5. Histological analysis of the middle medial condyle of 3-month goats that received an intraarticular injection of sodium hyaluronan (HA-treated group) or intraarticular injection of MSCs suspended in sodium hyaluronan (HA+MSC-treated group). Transverse sections of the middle medial condyle from HA-treated goats (n=3, left panels) and from HA+MSC treated goats (n=6, center and right panels). The arrows point to osteophytes.

This example describes the histological analysis of the medial middle condyle of 3-month goats that received intraarticular injection of sodium hyaluronan or intraarticular injection of MSCs suspended in sodium hyaluronan (HA-FMSC treated group). Transverse sections of the middle medial condyle from HA-treated goats (n=3, left panels) and from HA+MSC treated goats (n=6, center and right panels) are shown in FIG. 5.

The distal femur taken from the knee joint of treated and control animals was examined histologically. Transverse sections of the middle medial condyle from all operated joints from goats sacrificed at 3 months are shown. Sections from the contralateral joints of these animals were all histologically normal.

In the three HA-treated joints several structural changes were evident. These included (1) thickening of the subchondral bone plate, (2) reorganization of trabecular bone, (3) formation of medial osteophytes, and (4) fibrillation of the cartilage layer.

Osteophytes were particularly prominent in the control group (FIG. 5, left panel) and these are marked with an arrow. In the treated group, there was significantly less osteophyte formation associated with those joints where there was evidence of meniscal regeneration (FIG. 5, middle panel) and the condyles had a more symmetrical appearance, suggesting that they may have been less exposed to abnormal mechanical forces. The medial condyles from 2 of the 6 treated animals showed evidence of significant osteophyte formation (FIG. 5, right panel, marked with arrow). In these joints there was less evidence of formation of neomeniscal tissue.

Lesions in the articular layer were pronounced in the HA-treated group and can be seen as deep fissures (FIG. 5, left panel, top) or as erosion with loss of matrix staining (FIG. 5, left panel, bottom). In 4 of the 6 treated animals the cartilage layer was less damaged (FIG. 5, middle panel), although there was loss of surface staining (FIG. 5, middle panel, second from top) and some superficial fibrillation (FIG. 5, middle panel, third from top). Again, in 2 of the 6 treated animals there was significant damage to the cartilage including fissuring (FIG. 5, right panel, top) and erosion (FIG. 5, right panel, bottom), suggesting that there was little regeneration in these joints.

In the bone area immediately beneath the cartilage surface (the subchondral plate) there were some changes evident. In the untreated group (FIG. 5, left panel) there was evidence of plate thickening, as seen by more intense staining. This can be seen by comparing the left panel, top image with the center panel, top image, for instance, where the differences in plate thickening are evident. In addition there were changes within the trabecular bone suggesting that the trabecular were thicker and closer together in the untreated group (FIG. 5, left panel) compared to the treated group (FIG. 5, center and right panels). In 2 out of 6 animals in the treated group there were substantial bony changes (FIG. 5, right panel). As mentioned previously these animals had less neomeniscal tissue formation compared to the others.

EXAMPLE 4

Introduction

The purpose of this experiment was to demonstrate the effect of administration of MSCs derived from an unmatched donor in a model of knee injury in the goat. In this case, injury to the stifle joint was created by complete medial meniscectomy without ACL resection, a procedure that has been shown to cause degenerative changes in the joint similar to osteoarthritis. No immunosuppressive therapy was given.

Methods

Study Design. The animals used in the study were castrated male Western cross goats (n=20) and were confirmed to be free of Q fever, brucellosis, and Caprine Arthritis Encephalitis. These were randomized into 4 groups that did not differ by age. Total unilateral medial meniscectomy was carried out and, after a 2-week recovery period, the animals were subjected to an imposed exercise regimen. The operated joint was treated by injection of a suspension of $10^7$ allogeneic MSCs in 5 ml of sodium hyaluronan (4 mg/ml) either 1 or 6 weeks after the surgical procedure. The three preparations of allogeneic donor cells were randomly distributed among the recipient animals. Control animals received 5 ml sodium hyaluronan without cells. The study design is summarized in Table 6.

Table 6. Study design for the evaluation of allogeneic MSCs in the treatment of knee injury resulting from complete medial meniscectomy (MMX).

TABLE 6

| Group | n | Surgical Procedure (unilat.) | Injection | Time of Injection (Wks) | Time to Sacrifice (Mo) |
|---|---|---|---|---|---|
| 1 | 5 | MMX | HA | 1 | 3 |
| 2 | 5 | MMX | HA | 6 | 3 |
| 3 | 5 | MMX | HA + MSC | 1 | 3 |
| 4 | 5 | MMX | HA + MSC | 6 | 3 |

The exercise regimen began two weeks after injection and was maintained until sacrifice at 12 weeks following the surgical procedure. Cranial to caudal and lateral radiographs of both stifles were taken prior to the initial surgery and at sacrifice.

Preparation of Cells. Vials containing the cryopreserved transduced allogeneic goat MSCs were thawed at 37° C. and washed with hMSC media. The cells were centrifuged for 5 min at 1500 rpm and 20° C. and resuspended in 10 ml PBS. 50 µl cell suspension was removed for determination of viable cell count using Trypan Blue. After a second PBS wash (20 ml), $10 \times 10^6$ cells were pelleted in a 50 ml sterile tube and resuspended in 5 ml Hyalartin V (4 mg/ml) using a 12-ml syringe with an 18 ga. needle.

Injection. Prior to injection of cells into the operated knee joint, goats were weighed and a blood sample was collected to obtain serum. The area around the knee was sterilized and placed in 70-90 degrees of flexion and flexed and extended 20 times to circulate synovial fluid throughout the articular space. As much fluid as possible was aspirated from the proximal trochlear groove. An 18-ga. needle was inserted posterior to the medial edge of the patellar ligament, through the triangle formed by the epicondyle of the femur, the meniscal/tibial plateau and the notch formed by their junction. A syringe containing the cell suspension was attached to the needle and the cell suspension injected into the joint capsule. The joint was flexed and extended 20 times and the goat was maintained in the prone position for approximately 10 minutes as anesthesia was removed. The animals were taken to a holding pen when there was evidence of recovery and normal breathing. The goats were then returned to free range.

Exercise The exercise regimen consisted of 12 runs on a circular track of outside circumference of 28.6 m and inside circumference of 16.3 m. This was carried out once a day, five days per week.

Tissue Collection. The operated and contralateral joints were harvested by disarticulation at the hip, photographed and evaluated for macroscopic changes. The joints were then fixed in formalin and were photographed and re-examined after fixation to confirm grading scores and to note the presence of osteophytes.

Results

Gross evaluation of joints on sacrifice showed the presence of repair tissue associated with the posterior medial compartment in joints treated with allogeneic MSCs (FIG. 6). This repair tissue appeared to be hyaline in nature and detached from the tibial plateau so that a bearing surface was established. Control (sodium hyaluronan only-treated) animals had evidence of synovial proliferation of this site, which was generally attached to the proximal tibia with minimal extension into the articulating surfaces.

Conclusion

These observations suggest that treatment of the meniscectomized knee by direct injection of a suspension of allogenic MSCs results in the rapid organization of a neomeniscal tissue and the potential for chondroprotection. Direct injection of allogeneic MSCs to the joint space may therefore be applied in the treatment of joints damaged, for example, as a result of meniscal injury.

The disclosures of all patents, publications (including published patent applications), and database accession numbers are incorporated herein by reference to the same extent as if each patent, publication, and database accession number were specifically and individually incorporated by reference.

It is to be understood, however, that the scope of the present invention is not to be limited to the specific embodiments described above. The invention may be practiced other than as particularly described and still be within the scope of the accompanying claims.

The invention claimes is:

1. A method of repairing damaged meniscal tissue in a joint of a human, comprising:
    administering directly to said joint via intra-articular injection a liquid suspension comprising isolated allogeneic mesenchymal stem cells and an acceptable pharmaceutical carrier in an amount effective to repair damaged meniscal tissue in a joint of the animal, wherein the mesenchymal stem cells differentiate into and/or stimulate production of meniscal tissue,
    wherein the suspension is administered in the absence of a scaffold and wherein the pharmaceutical carrier is saline.

2. The method of claim 1, wherein said mesenchymal stem cells differentiate into meniscal tissue.

3. The method of claim 1, wherein said suspension does not contain hyaluronan or a hyaluronic acid derivative.

4. The method of claim 1, wherein said joint is selected from the group consisting of knee, shoulder, and temporal mandibular joints.

5. The method of claim 1, wherein the mesenchymal stem cells are present in the liquid suspension in an amount of from about $1 \times 10^4$ cells to about $1.5 \times 10^8$ cells.

6. A method of reducing joint pain in a human, comprising:
   administering via intra-articular injection a liquid suspension comprising isolated allogeneic mesenchymal stem cells and an acceptable pharmaceutical carrier in an amount effective to reduce joint pain, wherein the mesenchymal stem cells differentiate into and/or stimulate production of meniscal tissue, wherein the suspension is administered in the absence of a scaffold and wherein the pharmaceutical carrier is saline.

7. The method of claim 6, wherein said mesenchymal stem cells regenerate meniscal tissue between opposing bone or osteochondral surfaces.

8. The method of claim 6, wherein said suspension does not contain hyaluronan or a hyaluronic acid derivative.

9. The method of claim 6, wherein said joint is selected from the group consisting of knee, shoulder, and temporal mandibular joints.

10. The method of claim 6, wherein the mesenchymal stem cells are present in the liquid suspension in an amount of from about $1 \times 10^4$ cells to about $1.5 \times 10^8$ cells.

11. A method of preventing osteoarthritis at a site damaged by meniscal injury in a human, comprising:
    administering via intra-articular injection a liquid suspension comprising isolated allogeneic mesenchymal stem cells and an acceptable pharmaceutical carrier in an amount effective to prevent osteoarthritis at the site, wherein the mesenchymal stem cells differentiate into and/or stimulate production of meniscal tissue, wherein the suspension is administered in the absence of a scaffold and wherein the pharmaceutical carrier is saline.

12. The method of claim 11, wherein said mesenchymal stem cells regenerate meniscal tissue between opposing bone or osteochondral surfaces.

13. The method of claim 11, wherein said suspension does not contain hyaluronan or a hyaluronic acid derivative.

14. The method of claim 11, wherein said site is selected from the group consisting of knee, shoulder, and temporal mandibular joints.

15. The method of claim 11, wherein the mesenchymal stem cells are present in the liquid suspension in an amount of from about $1 \times 10^4$ cells to about $1.5 \times 10^8$ cells.

16. A method of protecting articular cartilage at a site damaged by meniscal injury in a human, comprising:
    administering via intra-articular injection a liquid suspension comprising isolated allogeneic mesenchymal stem cells and an acceptable pharmaceutical carrier in an amount effective to protect articular cartilage at the site, wherein the mesenchymal stem cells differentiate into and/or stimulate production of meniscal tissue, wherein the suspension is administered in the absence of a scaffold and wherein the pharmaceutical carrier is saline.

17. The method of claim 16, wherein said suspension does not contain hyaluronan or a hyaluronic acid derivative.

18. The method of claim 16, wherein said site is selected from the group consisting of knee, shoulder, and temporal mandibular joints.

19. A method of reducing osteophyte formation at a site damaged by meniscal injury in a human, comprising:
    administering via intra-articular injection a liquid suspension comprising isolated allogeneic mesenchymal stem cells and an acceptable pharmaceutical carrier in an amount effective to reduce osteophyte formation at the site, wherein the mesenchymal stem cells differentiate into and/or stimulate production of meniscal tissue, wherein the suspension is administered in the absence of a scaffold and wherein the pharmaceutical carrier is saline.

20. The method of claim 19, wherein said suspension does not contain hyaluronan or a hyaluronic acid derivative.

21. The method of claim 19, wherein said site is selected from the group consisting of knee, shoulder, and temporal mandibular joints.

* * * * *